United States Patent
Robinson

(10) Patent No.: US 6,938,639 B1
(45) Date of Patent: Sep. 6, 2005

(54) DISPOSABLE FLUID CONTROL ISLAND

(75) Inventor: Allan R. Robinson, Minneapolis, MN (US)

(73) Assignee: Promethean Medical Technologies, Saint Anthony, MN (US)

(*) Notice: Subject to any disclaimer, the term of this patent is extended or adjusted under 35 U.S.C. 154(b) by 0 days.

(21) Appl. No.: 09/562,064

(22) Filed: May 1, 2000

Related U.S. Application Data

(63) Continuation-in-part of application No. 09/020,708, filed on Feb. 9, 1998, now Pat. No. 6,568,419.
(60) Provisional application No. 60/174,617, filed on Jan. 5, 2000.

(51) Int. Cl.[7] ............................ A61M 1/00; A61B 19/08; F16L 55/07
(52) U.S. Cl. .................... 137/312; 128/849; 128/855; 137/1; 137/362; 137/561 R; 137/602; 141/86; 141/88; 220/571; 604/356
(58) Field of Search ................................ 137/312, 602, 137/561 R; 4/581, 582, 583; 5/606, 620, 630; 184/1.5; 220/571; 222/108; 256/97.23; 604/356; 128/849, 853

(56) References Cited

U.S. PATENT DOCUMENTS

| | | | | |
|---|---|---|---|---|
| 3,503,391 A | * | 3/1970 | Melges | 604/356 |
| 3,757,356 A | * | 9/1973 | Freeman | 604/356 |
| 4,598,458 A | * | 7/1986 | McAllester | 604/356 |
| 4,679,590 A | * | 7/1987 | Hergenroeder | 137/312 |
| 4,690,137 A | * | 9/1987 | Starzmann | 604/356 |
| 4,729,404 A | * | 3/1988 | Hergenroeder | 137/312 |
| 4,889,155 A | * | 12/1989 | Trotter, Sr. | 137/312 |
| 4,890,628 A | * | 1/1990 | Jackson | 604/356 |
| 5,002,069 A | * | 3/1991 | Thompson et al. | 604/356 |
| 5,199,457 A | * | 4/1993 | Miller | 137/312 |
| 5,349,965 A | * | 9/1994 | McCarver | 604/356 |
| 5,452,739 A | * | 9/1995 | Mustee et al. | 137/312 |
| 5,738,139 A | * | 4/1998 | DeChard | 137/312 |
| 5,827,246 A | * | 10/1998 | Bowen | 604/356 |
| 5,845,641 A | * | 12/1998 | Pinney et al. | 604/356 |

* cited by examiner

*Primary Examiner*—George L. Walton
(74) *Attorney, Agent, or Firm*—Schwegman, Lundberg, Woessner & Kluth, P.A.

(57) ABSTRACT

A system and method for collecting distending medium or other fluids discharged during surgical procedures is shown. Also shown is a method for reducing the risk of hyponatremia. The apparatus makes it practical to determine the amount of distending medium retained by a patient during hysteroscopic or other surgical procedures, particularly procedures using non-isotonic distending medium during monopolar electrosurgery. The apparatus and methods are also useful during a variety of laparoscopic, obstetric, cardiovascular, liposuction, plastic, orthopedic, restorative, and other procedures.

44 Claims, 12 Drawing Sheets

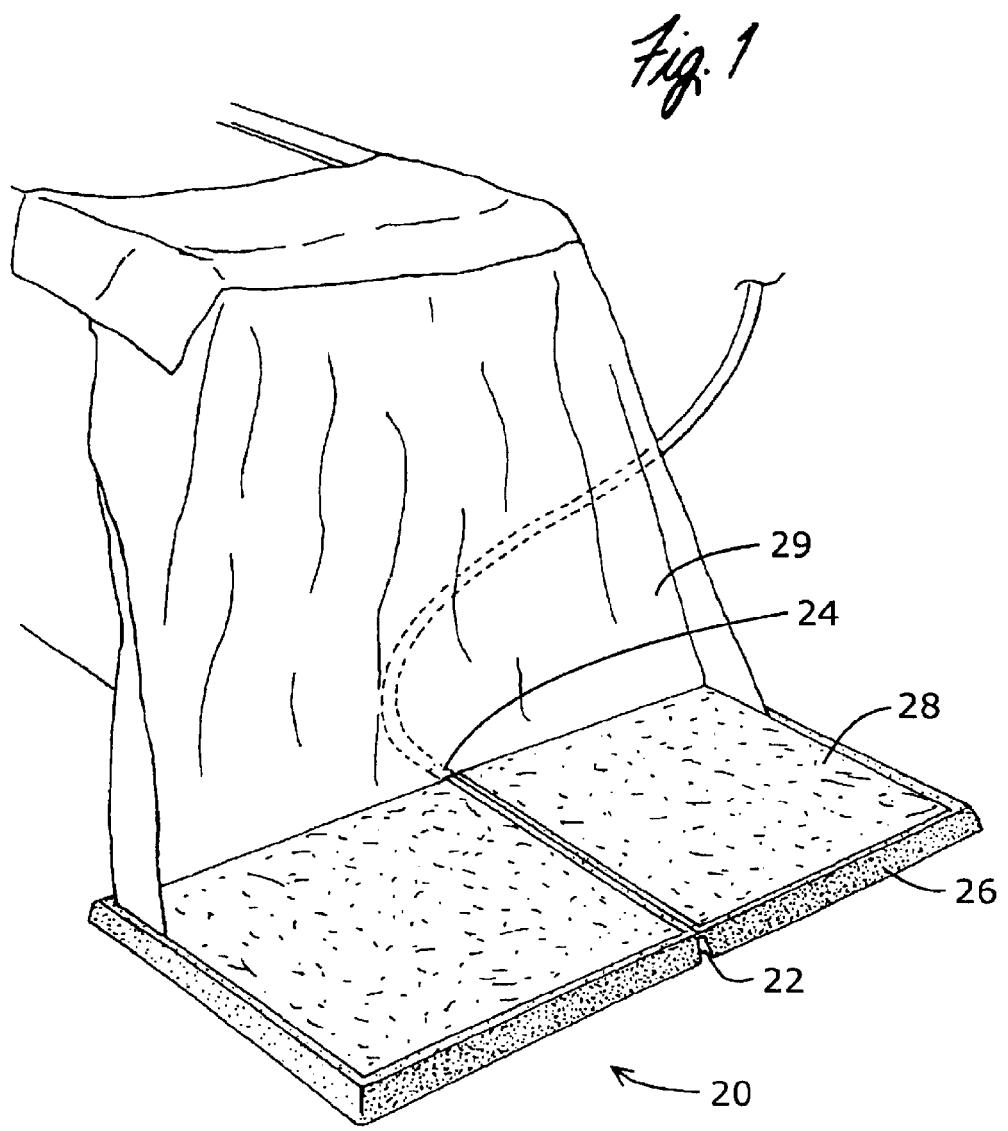

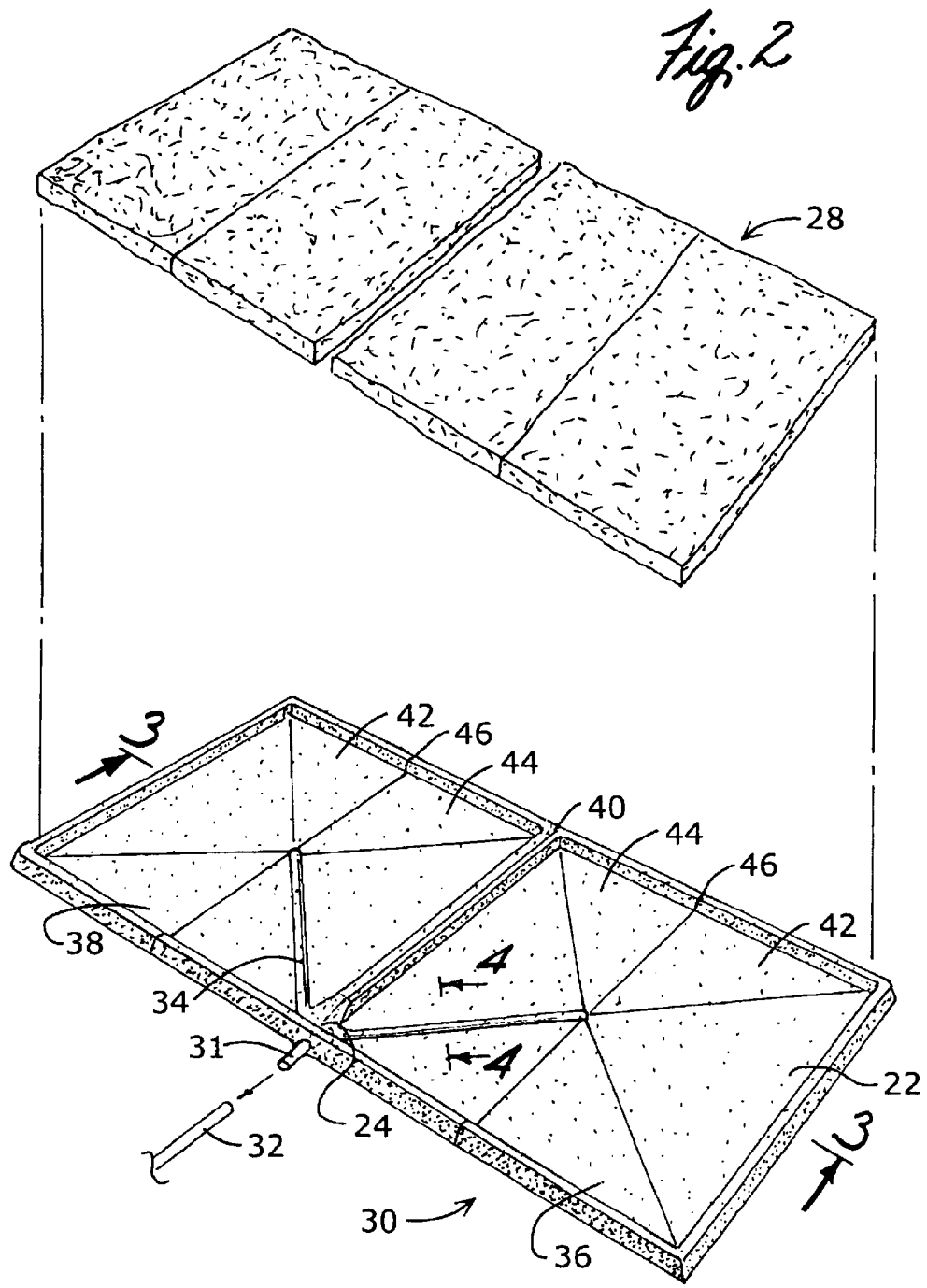

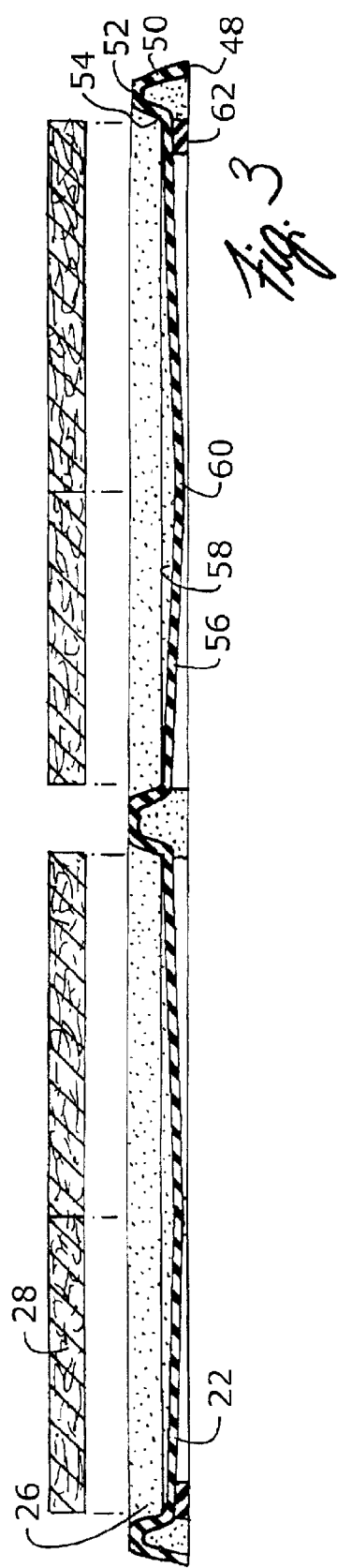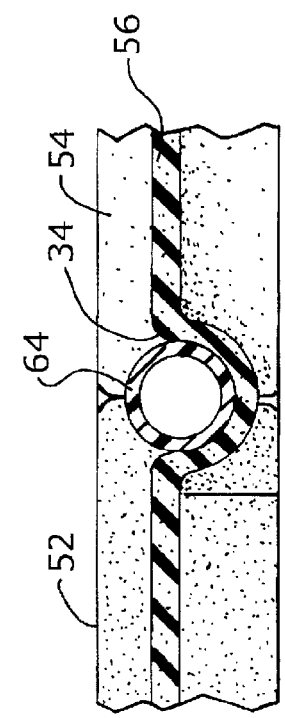

DISPOSABLE FLUID CONTROL ISLAND

REFERENCE TO PREVIOUS APPLICATION

This application is a Continuation-in-Part of application Ser. No. 09/020,708, filed Feb. 9, 1998 now U.S. Pat. No. 6,568,419. In addition, this application is based on Provisional Patent Application No. 60/174,617, filed Jan. 5, 2000.

TECHNICAL FIELD

The present invention relates to methods and apparatus for control of fluids in work areas. More specifically, the invention relates to methods and disposable apparatus for collecting fluids emanating from a work area. In particular, the present invention provides apparatus and methods for collecting and quantifying the amount of infused and bodily fluids released during surgical procedures, for example during hysteroscopy procedures.

BACKGROUND

A problem affecting the health and safety of a variety of workers is that of providing a safe, non-slippery, dry area upon which the workers can stand. Hospital operating room personnel are routinely required to stand and work in conditions in which the floor is inundated with several liters of blood, bodily fluids, and saline or other solutions during a single procedure. The abundance of fluids released during surgery is due in part to refinements and widespread implementation of improved surgical techniques during recent years.

In U.S. Pat. No. 4,635,913, issued Jan. 13, 1987; U.S. Pat. No. 4,718,653, issued Jan. 12, 1988; and U.S. Pat. No. 4,811,937, issued Mar. 14, 1989, Rothman disclosed a series of Portable Surgical Drainage Platforms. The inventions he developed could assist surgeons and other surgical staff by supporting the personnel on grating and removing liquid that falls through the grating. The platforms are, however, rather heavy and are also difficult to sterilize, especially in the limited amount of time that may be available between surgeries.

LaRooka received U.S. Pat. No. 4,243,214 on Jan. 6, 1981, for her Irrigation-Debridement-Repair Caddy. That disclosure is directed to an apparatus that can be placed under an extremity of a person during a surgical procedure. The Irrigation-Debridement-Repair Caddy is designed to collect some of the irrigation distending medium and excised tissue that would otherwise drip onto the floor and collect the fluid in a closeable bottle for eventual disposal.

Other devices such as the AquaVac mat marketed by Arthroplastics of P.O. Box 332 Chagrin Falls, Ohio 44022 appear to be directed primarily toward removing water from floors rather than quantifying the amount of fluid received from a patient in order to determine whether the patient's condition is satisfactory.

Clear saline solution or nonelectrolytic distending medium infused into the region where surgery is being conducted allows the surgeon to see the affected tissue much more clearly than would otherwise be possible. In addition, the distending medium can separate and stabilize the tissue to improve surgical precision and reduce the time required to carry out procedures.

Among the problems engendered by dispersal of infused fluids and blood onto operating room tables and floors are the considerable inconvenience to workers, the increased likelihood of contamination, the potential for spread of infectious disease, More importantly, distending medium is used in hysteroscopic, urologic, and possibly other surgical procedures that, if taken up by the patient, increase risk of complications. A patient can suffer serious, or even fatal, complications by absorption of distending medium that is suffused into the area where the surgery is conducted by the hysteroscope. The amount of distending medium that a patient can absorb without intolerably dangerous adverse effects is related in non-intuitive ways to various individual physical, chemical, and other factors. The perioperative nurse will, before the patient arrives in the operating room, make a reasonable estimate of the amount of distending medium that a specific patient can tolerably absorb by factoring the person's age, weight, fitness, hormonal balance, the formulation of the distending medium, the procedure being performed, and a host of other variables. Unfortunately, the maximum usefulness of that estimate can be realized only if the amount of fluid the patient retains can be timely determined with sufficient accuracy while the procedure is carried out.

The quantity of infusion fluids absorbed by a patient naturally increases with the length of time required to perform the procedure. Hospitals, surgeons, and patients normally seek to conclude the surgery as quickly as possible for good reasons. Other things being equal, the less time required to perform a surgery, the better the expected outcome and the quicker the patient is expected to recover.

Infusion fluids are taken up by the patient more rapidly during some procedures, compared to others. Sometimes infusion fluids are absorbed so rapidly that the surgeon may not have enough time to address and correct all of the problems and complexities discovered during the surgery. In such instances, it might be necessary to terminate a procedure when only a few additional minutes of the surgeon's time would be sufficient to complete the process as desired. That is a very undesirable situation because patients in those cases must be allowed to recover in the hospital for several days and then, often in a weakened condition, again be prepared, anesthetized, and the surgery resumed. Because those additional risks are widely recognized, as is the risk of continuing a surgery when a patient may, or may not, be in danger from excessive absorption of infusion fluids, the surgeon, lacking accurate information, is forced to make a decision that can easily be criticized in hindsight.

Based on these factors, it is easy to understand that surgeons, hospitals, and their patients would be greatly assisted by more accurate knowledge of the amount of infusion fluids retained by surgical patients. Although infusion fluids may accumulate in the abdomen or the patients extremities, the greatest concern is for accumulation and absorption of infusion fluids during surgeries in which severed veins are exposed to infusion fluids. Hysteroscopic and, to a lesser extent, urologic procedures performed using monopolar electrosurgery inherently give rise to conditions that can quickly lead to dangerous complications if any member of the surgical team is unable to maintain a vigilant lookout for the onset of hyponatremia.

The hazards of hyponatremia are widely recognized by workers throughout the fields of obstetrics and gynecology. Although the medical literature has many excellent publications addressing the problem in varying breadth and depth, a good overview explaining the subject and the causation of the potential harms is presented by Donna Morrison, R.N. in her article "Management of Hysteroscopic Surgery Complications," J. Assoc. of Operating Room Nurses, vol. 69, No. 1, Jan. 1999, pp.□194–209. Morrison explains that dilutional hyponatremia is a complication of hysteroscopic surgery that is associated with intravasation of a low viscosity nonelectrolytic distending medium. Women are more likely than men to suffer dilutional hyponatremia, and premenopausal women are 26 times more likely than postmenopausal women to encounter hyponatremia. Premenopausal women are at greatest risk, then, usually as the result of hysteroscopic procedures; the same considerations are, however, important in urologic, and perhaps other procedures that may be undertaken on either male or female patients. For the convenience of the reader, it is to be understood that references to hysteroscopy and hysteroscopic procedures are intended to include urology, urologic, and urological procedures, and any other type of surgical procedure that exposes the patient to risk of hyponatremia or in which it would be helpful to know the volume of fluid retained by a patient.

The distending medium, or infusion fluid used in electrosurgery has lower osmotic potential, or tonicity, than the patient's tissues, serum, and intercellular fluids. For that reason, the distending medium is absorbed fairly quickly by the tissues surrounding the surgical site. Not only is the distending medium absorbed quickly by osmosis, the fluid is supplied under pressure in order to distend the area where the surgery is being performed to enable the surgeon to repair damaged tissue with greater speed and precision. The pressure needed to distend the area can exceed the patient's blood pressure thereby actively forcing distending medium to flow into blood veins that are cut or broken in the course of the surgery. Free water can enter the vascular system through blood vessels and sinuses opened as the integrity of the endometrial lining or other tissue is interrupted during surgery.

Efforts to cauterize exposed vasculature are maintained throughout the surgery, however the process is not instantaneous, and some distending medium will be forced into the patient's circulatory system as a result. The duration of the surgery must be limited for that reason, even under the best of circumstances. As a practical matter, undetected damage to vessels or other tissue exposed to the pressurized distending medium will sometimes be present, vasculature thought to have been cauterized may subsequently begin to admit distending medium, or other sub-optimal conditions may develop. Any event or condition that increases the patient's uptake of distending medium necessarily shortens the permissible duration of the surgical procedure.

If that were the extent of the problem, a patient in that situation might merely need to endure a period of uncomfortable puffiness. However, the brain, like the rest of the patient's tissue, seeks to balance the ionic strength of the diluted blood by removing water from the blood and adding that water to the brain tissue. The skull provides scant room for the brain to expand as it swells from the added water; extreme pressure can build fairly quickly. Brain stem herniation can develop as the brain expands attempting to equalize interstitial and intervascular osmotic pressures. Morrison reports that this condition, hyponatremic encephalopathy, has high morbidity and mortality rates and may result if dilutional hyponatremia is not recognized at its onset and treated promptly. She, like many other observers of the problem, recommends that operating room personnel regularly monitor the amount of distending medium the patient receives and the amount returned because that is the quickest way to detect possible intravasation caused dilutional hyponatremia.

To that end, surgeons often request the operating room personnel to report the amount of fluid that has been introduced into and received from the patient. Fluid limits are normally fixed between 500 ml and 1,500 ml., and surgery time is frequently limited to one hour. Unfortunately, it is difficult to reliably measure the volume of distending medium received from the patient using traditional methods and equipment. Likewise, It is difficult to measure the volume of fluid infused with traditional methods and equipment.

Operating room personnel will know with certainty the number of 3 liter bags of distending medium that have been infused at any particular time. Beyond that, there has been little certainty available. To estimate the amount remaining in a partially used 3 liter container of distending medium, it is usually necessary to remove the bag from the pressurizing cuff or collar in which it is located during use. Of course, removing the pressurizing collar halts the flow of distending medium to the location of the surgery which can quickly interrupt the conduct of the procedure. Once the uncalibrated, shapeless 3 liter bag is visible, operating room personnel would then estimate (i.e. guess at) the amount remaining in it. The amount of infusion fluid discharged from the hysteroscope outflow would normally be collected, and therefore measurable. Careful draping can direct some of the returned fluid into kick buckets, but some is likely to disperse onto the operating room floor, the table, and into pads or towels. The difference between the amount of fluid introduced and the amount of fluid collected or dispersed onto the operating table and floor gives some estimation of the amount of fluids remaining in the patient. Such estimates are crude approximations at best, and generally recognized as such by the persons making and using them.

A cross check may be provided by measuring serum sodium concentration during the surgery both periodically and whenever intravasation is suspected.

If the surgical team discovers that intravasation has occurred, the situation must be treated as an emergency requiring the surgeon to halt the procedure as soon as it is safe to do so. Electrolytes, oxygen, and other treatments would be administered as quickly as possible.

It is readily appreciated that the consequences of underestimating the amount of infused fluid taken up by the patient can include morbidity and mortality. Underestimating the amount of fluid received from the patient can result in premature termination of surgery and can instigate an emergency response that imposes additional risk upon the patient.

In an effort to determine the reliability of the estimates of fluid balance that operating room personnel make, a preliminary test was conducted by one hospital to evaluate the accuracy of visual estimates of fluid volumes experimentally. Four experienced operating room nurses were each asked to visually estimate fluid volumes under nineteen different conditions: the amount of distending medium remaining in ten different 3 liter bags; the amount of fluid received in four different kick buckets; and the volume of fluid present on five different operating room floors. The results of the experiment are presented in Table 1. Although the individuals were experienced, trained, and capable in their fields, their estimates of fluid volumes deviated from the actual amounts sufficiently to risk premature cessation of a surgical procedure in most instances. Participants underestimated the amount of fluid present regularly. Out of 76 estimates 74 were less than, and only two exceeded, the actual liquid volume. The errors are additive, and effect of the cumulative errors is that, even if only the best estimate from each trial is considered, in more than 75% of the cases, a recommendation to halt the surgery is indicated by these estimates, even if absolutely no distending medium had been retained by the patient.

In the effort to more accurately evaluate the amount of distending medium returned by the patient, surgical drapes may be arranged to direct the returned fluid to buckets positioned on the floor. It can be necessary to halt the surgery while the unsterile contents of the buckets are measured. But, as can be seen from studying Table 1, the estimation errors for the amounts of fluid on the operating table and on the floor can be so large that there is little value in knowing the volume of fluid accumulated in the kick buckets.

What is needed is a practical way to collect fluids returned from a patient during hysteroscopic surgical procedures.

Also needed is a way to measure the volume of fluids returned from a patient during hysteroscopic surgery.

A further need is for apparatus whereby it is possible to determine the volume of distending medium that has been infused into a patient.

Yet another need is for the ability to quickly learn the difference between the amount of distending medium that has been infused into the patient and the amount of distending medium that has been returned from the patient.

SUMMARY

Previously known methods and apparatus have been unable to implement a solution to the various problems encountered by people who work in areas where wet floors are routinely encountered. In hospital operating rooms, for example, the method for controlling wet floor problems is often merely to scatter disposable absorbent blankets, pads, or mats on the floor. Following the surgery, the absorbent material may be weighed to measure the amount of fluid lost by the patient during the procedure. Typical absorbent blankets are made of materials similar to those used to make disposable diapers. It may readily be appreciated that standing, walking, and working with several pieces of that type of material disintegrating on the floor surface is difficult, at best. Unfortunately, those activities are especially difficult under actual conditions because the considerable activity during a surgical procedure tends to bunch up the absorbent materials. It can be appreciated that these circumstances are not conducive to obtaining information about the amount of distending medium that may have been introduced into the patient's vasculature.

What is needed, then, is a disposable fluid control island for selectably collecting, retaining and draining fluids received from hysteroscopic surgery patients comprising a generally broad, shallow, impermeable vessel having a generally horizontal, floor-contacting, bottom portion and a generally vertical peripheral portion, a foot-supporting portion disposed within and substantially filling the vessel, the splash-preventing portion having a top surface spaced apart from the vessel bottom portion by filler comprised of nonwoven, nonabsorbent polymer fiber mesh, and a liquid retaining portion comprised of fluid-permeable material, and means for allowing fluids to be removed from the apparatus for measurement and, when necessary, additional analyses.

It is possible to fabricate the mesh in specific colors to accomplish additional purposes. For example, using a white mesh can make it easier for operating room personnel to determine that blood is escaping from the patient. It may also be possible to coat the fibers of the non-woven mesh with indicator dyes that would alert operating room personnel to the presence of substances of concern.

Embodiments of the present disclosure meet these needs, and more, by solving the long-recognized problem of containing and removing fluids received from hysteroscopic surgery patients so that the volumes of the fluids can be measured. The present disclosure teaches a disposable, fluid containing and draining vessel filled with macro-porous material having substantial void space that quickly directs fluids to a receptacle for quantification. In a preferred embodiment, the porous supporting and or filler material is a stiff, hydrophobic, non-woven, polymer fiber mat that has substantial void space. Many other configurations for the supporting material may be used without departing from the scope of this disclosure. It is believed that the non-woven polymer mat has superior splash preventing properties compared to other types of matting or mesh.

The support material preferred, however, is lightweight so that the fluid control island may be shipped, stored, and handled easily by personnel who have no special training, physical abilities or equipment. It is also preferred that the support material be inexpensive so that the fluid control island can be disposed of destructively to reduce the potential for environmental and health hazards that might result from attempts to clean and re-use the components. It is also preferred that the support material have good shelf life. Other desirable support material characteristics include: that it is non-slippery when wet, that it remains flat on the floor surface while the fluid control island is in use, that liquids may be readily removed from the support material for recovery or analysis, that it be easily bonded to the vessel material, that it does not cause allergic reactions, that it does not create difficult disposal problems, and that it can be folded or rolled for shipping.

The support material is contained within a shallow vessel that prevents fluids that fall onto the support material from contacting the floor. The vessel may be formed in many different configurations, however, it may be most useful when it substantially covers the area between the surgeon and the operating table. Since the surgeon would normally be seated near the patient and observing the surgery on a video monitor, an appropriate size for the vessel is approximately 17"×34", but could be any other size without departing from the scope of this disclosure.

The fluid control island vessel may have a mesh thickness of about ¼" to ¾" with a drainage slope of about ¾" over the length and/or the width. The drainage slope causes the liquid to flow toward one end or region of the vessel making it possible to remove essentially all of the fluid, with very little remaining on vessel or mesh surfaces. Evacuation of the vessel can easily be accomplished with either a vacuum source and fluid collection canisters or with use of a pump capable of pumping the specific liquids that a particular vessel collects. Such a fluid control island vessel, with the support mat in place, can contain a substantial volume of fluids giving the system a surge capacity that makes it possible to use a relatively low rate of fluid removal with an inexpensive removal system, whether vacuum operated or pumped directly, yet still have sufficient capacity to collect and remove all the fluids collected in the vessel during a procedure.

The base of the disposable fluid control island may be furnished with sloping transition members that make the change in elevation from the fluid control island to the floor gradual. The vessel may also be made from generally pliable material such as foamed polyurethane so that the peripheral walls of the vessel could compress or bend to conform to the presence of personnel or apparatus. It is also to be understood that the vessel may be comprised of a disposable liner and mesh pad combination that can be fitted into a more substantial receiving element. Such a receiving element could be portable or, in the case of areas or rooms where the disposable fluid control island is used frequently, it could be comprised of floor Indentations sized to receive the disposable fluid control island vessel with minimal difference in the elevation of the support surface and the surrounding floor.

It is believed that the integration of surgical drapes with the hysteroscopy fluid control island can enable hysteroscopic surgeons to use general operating rooms to perform hysteroscopic surgeries rather than being restricted to operating rooms that are specially equipped for hysteroscopic surgery. This advantage could make it possible for patients and physicians to obtain hysteroscopic surgical services in many additional hospitals and clinics.

By collecting substantially all of the fluid received from a patient during hysteroscopic procedures, it is possible to know with previously unobtainable accuracy how much fluid is retained by a patient. However, it is also necessary to determine the amount of fluid introduced to the patient. In a further development of the invention, the container (usually a 3 liter flexible plastic bag) of distending medium, together with the pressure cuff that forces the fluid out of the container, is suspended from a scale that allows surgical personnel to determine the difference between the initial weight and the weight at any subsequent time. Conversion of the weight difference is straightforward since the density of the distending medium is known. The fluid received from the patient can be drawn into collection containers by house vacuum where it can be conveniently measured directly in calibrated containers. The fluid collected by the fluid control island may also be pumped to the collection containers. It would also be possible to determine the volume of collected fluid using a weighing system as described for the distending medium. It may also be possible to weigh the source fluid and the received fluid on the same scale to achieve an accurate measure of fluid remaining in the patient in real time. Another alternative method would be to measure the amounts of fluid introduced into and received from the patient with mass flow meters and compute the difference with electronic computing machinery to inform the surgical team of the amount of fluid retained by the patient.

BRIEF DESCRIPTION OF THE DRAWINGS

FIG. 1 is a perspective view showing a two-section disposable fluid control island with attached surgical drape and vacuum operated fluid removal provision.

FIG. 2 is an exploded view of a first alternative double bi-fold embodiment of a disposable fluid control island similar to the one shown in FIG. 1.

FIG. 3 is a cross-section of the embodiment of the disposable fluid control island of FIG. 2 taken at 3—3.

FIG. 4 is a cross-section of the embodiment of the disposable fluid control island of FIG. 2 taken at 4—4 showing the fluid-removing tubular vacuum conduit in greater detail.

DETAILED DESCRIPTION OF THE PREFERRED EMBODIMENT

Figure 5:
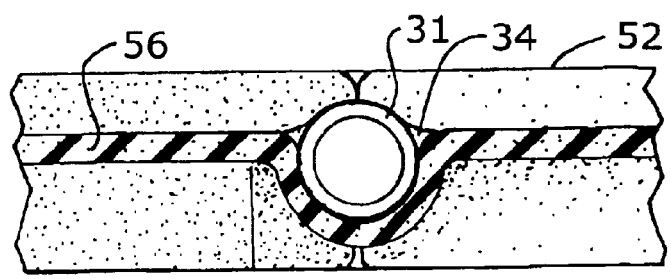
FIG. 5 is a cross-section of the embodiment of the disposable fluid control island of FIG. 2 taken at 4—4 wherein the fluid-removing conduit is an open-topped channel with a terminal vacuum connection fitting superimposed.

The construction of a fluid control island for hysteroscopic procedures may be understood viewing the accompanying FIG. 1 through FIG. 16, particularly in view of my co-pending patent application 09/020,708, the disclosure of which is incorporated herein by reference.

FIG. 1 shows, in perspective, a disposable fluid control island 20 for selectably collecting, retaining and draining fluids received from patients during surgery comprising: a generally broad, shallow, impermeable vessel 21 having a generally horizontal, floor-contacting, bottom portion 22 that is shaped to direct fluids that enter the vessel toward a drain portion 24 that extends through the vessel 21, the drain being adapted for connection to a fluid collection container. A generally vertical peripheral portion 26, retains a non-absorbent mesh pad portion 28 fitted within the peripheral portion 26 of the vessel and overlying the bottom portion 22 of the vessel 21. The non-absorbent mesh pad 28 may be a non-woven, textile fiber mesh, an open-cell polymer foam, or other, equivalent, structure that prevents or reduces fluid splatter, has a high ratio of void space, and that has low fluid retention. A surgical drape 29 may optionally be affixed to the fluid control island 20. The drape 29 may be attached to the peripheral portion 26 of the vessel along the side that is positioned closest to the operating table and continue perpendicularly along the ends of the vessel 22 for several inches. This configuration can effectively channel substantially all he fluid discharged during a surgical procedure into the fluid control island 20.

FIG. 2 is an exploded perspective view of an alternative double bi-fold embodiment 30 of a disposable fluid control island 20. It can be seen that the drain portion 24 may include a tubular portion, or bulkhead feed-through fitting 31, communicating between the vessel 22 and a means, such as a length of tubing 32, for conveying fluids that enter the vessel to at least one collection canister for measurement of the volume of fluids that are received by the vessel. House vacuum, a separate conventional vacuum pump or a small liquid pump may be used to convey fluids through the drain 24 and into collection canisters.

The bottom portion 22 of the vessel 21 may be inclined toward the drain 24. Optionally, channels 34 may be formed in the bottom portion 22 of the vessel to direct fluids toward the drain 24 and to reinforce the vessel structure.

In this double bi-fold embodiment 30, the bottom portion 22 is divided into a first bottom section 36 and a second bottom section 38 by a center hinge portion 40. Each section of the bottom portion is further divided into a distal part 42 and a medial part 44 that are connected by a bottom hinge 46. The mesh pad 28 may be subdivided corresponding with the bottom portion 22 and optionally affixed thereto.

FIG. 3 is a cross-section of the disposable fluid control island 30 taken at 3—3 of FIG. 2 showing the mesh 28 and vessel 21 in greater detail. The bottom 22 is shown sloping from the peripheral edge 26 to a lower region 36, shown in the center of the bottom portion in this embodiment. The peripheral edge 26 has a floor-contacting base 48 that may include adhesives, surface treatments, materials or finishes that impart desired properties, such as limiting slip, to the fluid control island 20. An outer wall 50 is connected by the top portion 52 to the inner wall 54 which bounds the generally planar panel 56.

The panel 56 has a panel upper surface 58 that can be configured to slope to a low point 60 where fluids accumulate for removal. The low point 60 may be in the center of the panel 56, or at any other convenient location. Spacers 62 may be situated to support areas of the panel 56 and to maintain the desired slope.

FIG. 4 is a cross-section of the disposable fluid control island of FIG. 2 taken at 4—4 showing an optional fluid-removing tubular vacuum conduit extension 64. When present, the vacuum conduit extension 64 may be positioned to extend to the location of a low point 60 from the bulkhead connection 31. The extension 64 could be fitted into a pre-formed channel 34 or held in place by adhesive or mechanical fasteners.

Fluids may be routed to the drain 24 through open-topped pre-formed channels 34 that do not contain a vacuum conduit extensions 64. FIG. 5 is a cross-section of an alternative embodiment of the disposable fluid control island of FIG. 2 taken at 4—4 wherein the fluid-removing conduit is an open-topped channel 34 with a terminal vacuum connection fitting 31 superimposed.

Figure 6:
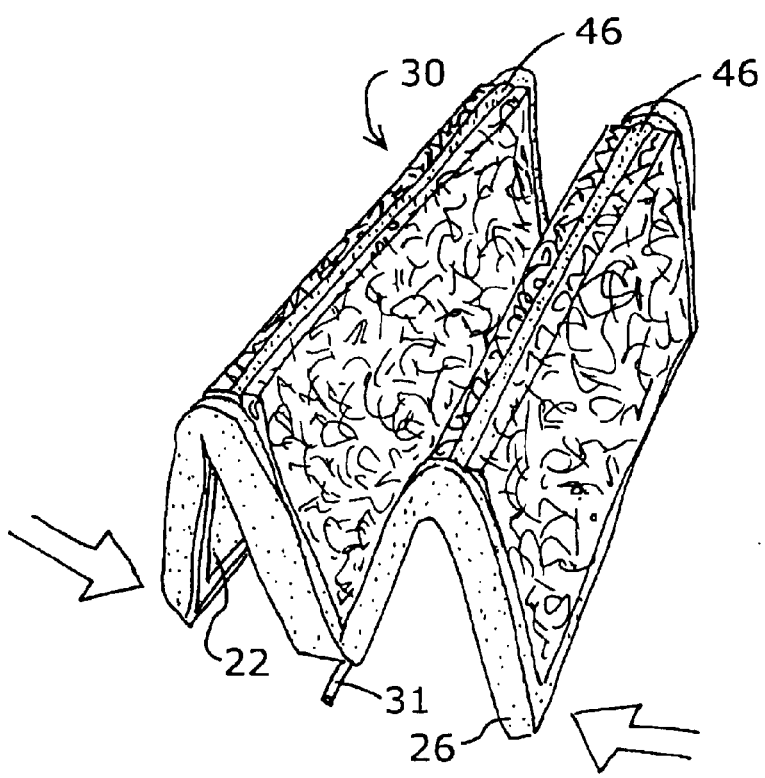
FIG. 6 is a respective view of the disposable fluid control island of FIG. 2 wherein the embodiment is shown being folded for disposal.

FIG. 6 is a perspective view of the double bi-fold embodiment of the disposable fluid control island 30 of FIG. 2 wherein the embodiment is shown being folded for disposal. The functions of the center hinge 40 and of the bottom hinges 46 are clearly revealed in this FIG. 6. It is to be appreciated that the fluid control island 30 can be quickly and easily folded so that the entire article will fit into a conveniently sized disposal container.

Figure 7:
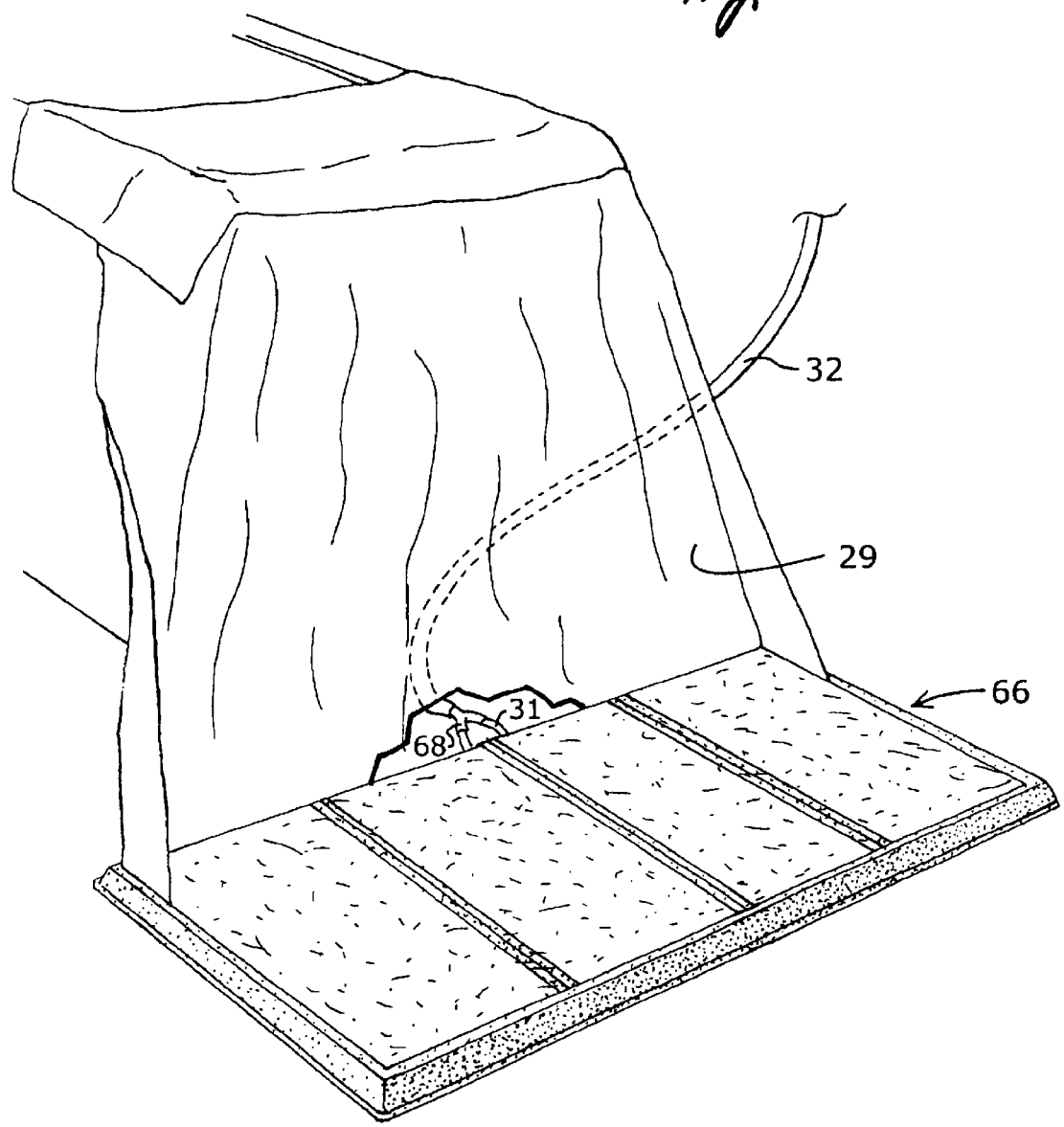
FIG. 7 is a perspective view of a second alternative embodiment of the disposable fluid control island of FIG. 2 wherein a surgical drape is affixed to the fluid control island to direct all fluids toward the vacuum fluid collection system.

FIG. 7 is a perspective view of an alternative surgical drape-equipped embodiment 66 of the disposable fluid control island of FIG. 2 wherein a surgical drape 29 is affixed to the fluid control island to direct all fluids toward the vacuum fluid collection system. An alternative drain 24 configuration is depicted wherein each medial part 44 is fitted with a bulkhead fitting 31. A "Y" connector 68 is used to connect both of the bulkhead fittings 31 to the conduit 32 that conveys fluids to collection containers.

Figure 8:
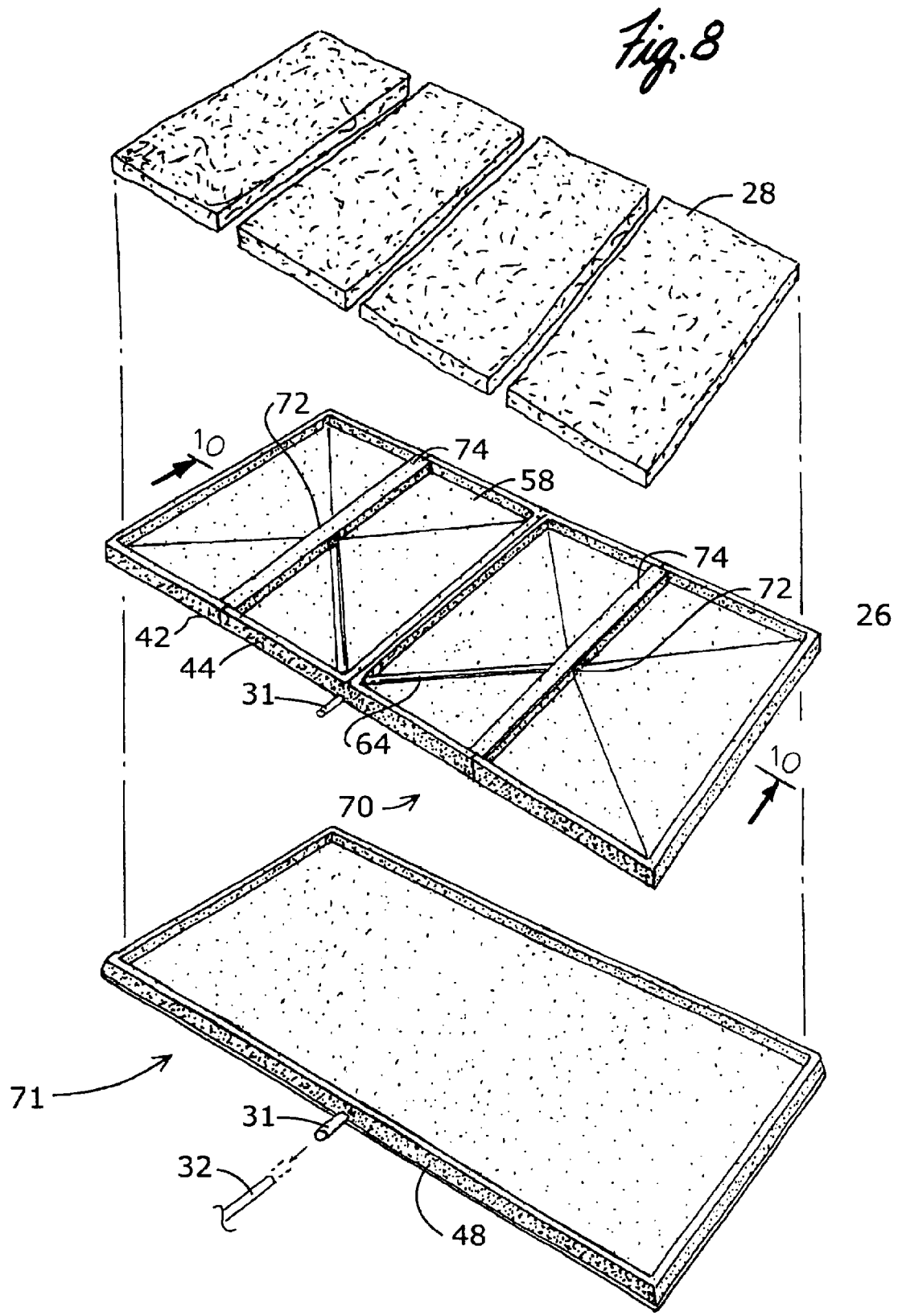
FIG. 8 is an exploded perspective view of a third alternative embodiment of a fluid control island that has a drain at the center of a long edge of each rectangular section of the island.

FIG. 8 is exploded perspective view of another alternative embodiment 70 of a fluid control island. An optional drain base 71 may receive a disposable fluid control insert 70 that has an extended drain inlet 72 at the center of a long edge of each rectangular bottom part 42 44 of the island. The drain base 71 may optionally be formed integrally with the disposable fluid control insert. It is to be understood that many embodiments of the subject matter disclosed herein can provide a working fluid drainage system for surgery that can enable surgeries to be performed in rooms that lack floor drains. That is particularly true in the configuration disclosed in FIG. 8 which provides a substantial structure for securely retaining lightweight, disposable fluid control inserts 70 that may be replaced following each patient surgery. As hospitals seek to maximize utilization of their resources, this feature makes it possible to increase the versatility of existing facilities during times of increased demand for surgical services and by eliminating the restriction on operating room design that may be imposed by the necessity of positioning apparatus with respect to floor drains. It is also possible that the article disclosed herein, in any of the disclosed embodiments and their equivalents, will be preferred as a fluid drainage system in place of floor drains because the disposable drain system 20 removes the fluids from the operating room for proper disposal (e.g., incineration) rather than as ordinary sanitary waste.

Advantages may result from using the fluid control apparatus and methods 20 disclosed here even if the availability of floor drains at desired locations in operating rooms imposes no restriction. This fluid control island is replaced anew before each surgical procedure, the used island being sealed and disposed of, together with other surgical debris. When fluids received from a surgical patient are collected with the present disposable island, there is no possibility that the drain can serve as a reservoir for pathogens, toxins, or other contaminants that might harm subsequent patients or health care professionals. An operating room floor drain, however, can be a reservoir of infectious microorganisms originating from previous surgical patients or even from sources external to the health care facility.

In addition his dual drain embodiment 70 shows an alternative method of construction. The bottom 22, including the peripheral edge 26, may be formed of solid foam material rather than from sheet foam material. Although this method of construction uses more material and is more costly as a result, it allows a steeper gradient on the upper surface 58 of the bottom panel. Extensions 64 reach the center of the junction of the distal 42 and medial 44 parts. This dual drain embodiment 70 is shown with optional solid foam dividers 74 between each rectangular distal part 42 and medial part 44. This type of construction may be selected, among other times, when it is desired to make the outer wall 50 angle gradually from the floor surface to the top of the peripheral edge 52. This configuration reduces the maximum distance between the peripheral edge 26 and drain to half that of the configuration depicted in FIG. 1 while simultaneously doubling the gradient of the bottom surface 58. These two factors hasten evacuation of fluid through the drain conduit is extension 64 and reduce the lag time between the cessation of fluid flow and the measurement of collected fluid volume.

Figure 9:
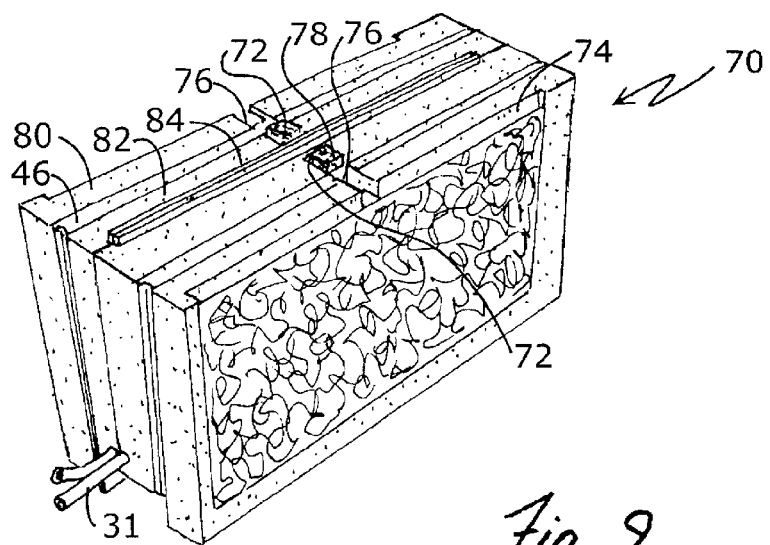
FIG. 9 is a perspective view according to FIG. 8 wherein the disposable fluid control island is folded for shipping, storage, or disposal.

FIG. 9 is a perspective view of the dual drain embodiment 70 according to FIG. 8 wherein the disposable fluid control island is folded for shipping, storage, or disposal. The dividers 74 may include a slot 76 and a filter block 78 near the center drains 72 to permit fluids to flow from the distal side 42 and be evacuated. The filter block 78 may be made from the same mesh as the pad 28 or other materials.

The mating face of the distal portion 80 can be brought into contact with the mating face of the medial portion 82 if the hinge 46 is fitted with sufficient precision. However, the faces 80 and 82 need not actually touch to obtain satisfactory operation of the fluid control island 70 because the center drains 72 withdraw fluids that might flow into the gap between the faces. An overlap 84 may be included to divert fluids from the vicinity of the faces 80 82 and toward the upper surface of the bottom 58 that is sloped toward the drains 72.

Figure 10:
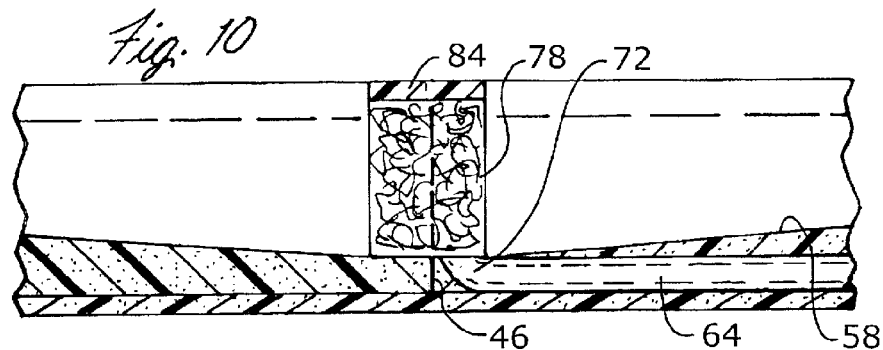
FIG. 10 is a section detail of the disposable fluid control island of FIG. 8 taken at 10—10.

FIG. 10 is a section detail of the disposable fluid control island 70 of FIG. 8 taken at 10—10 depicting one of the lateral, or bottom, hinges 46, drain 72, and filter block 78.

Figure 11:
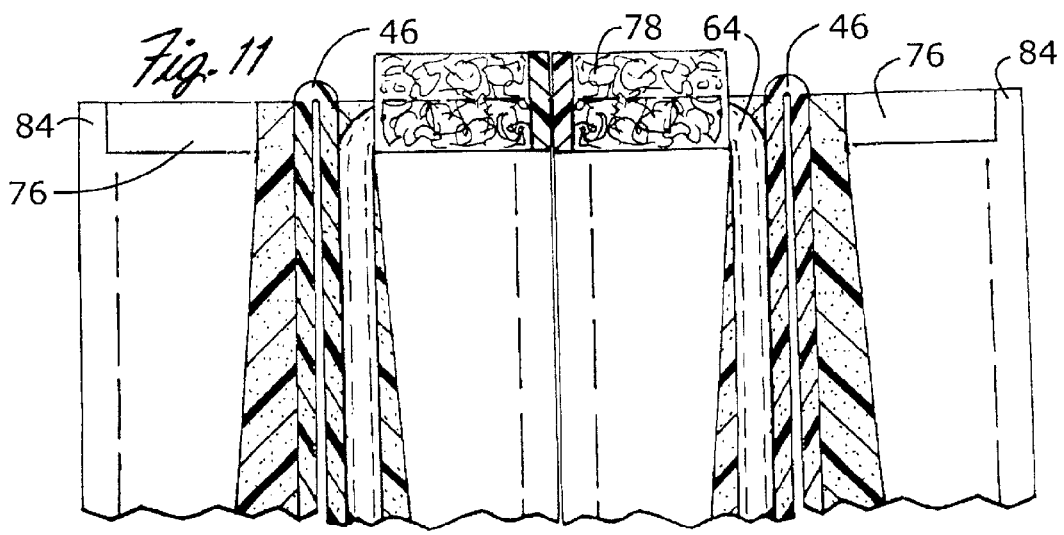
FIG. 11 is a section detail of the disposable fluid control island of FIG. 8 taken at 10—10 wherein the article is folded according to FIG. 9.

FIG. 11 is a section detail of the disposable fluid control island 70 of FIG. 8 taken at 10—10 wherein the article is folded according to FIG. 9. The mating relationship among the slot 76, the filter block 78 that fits into the slot, and the overlap 84 are readily seen in this figure.

Figure 12:
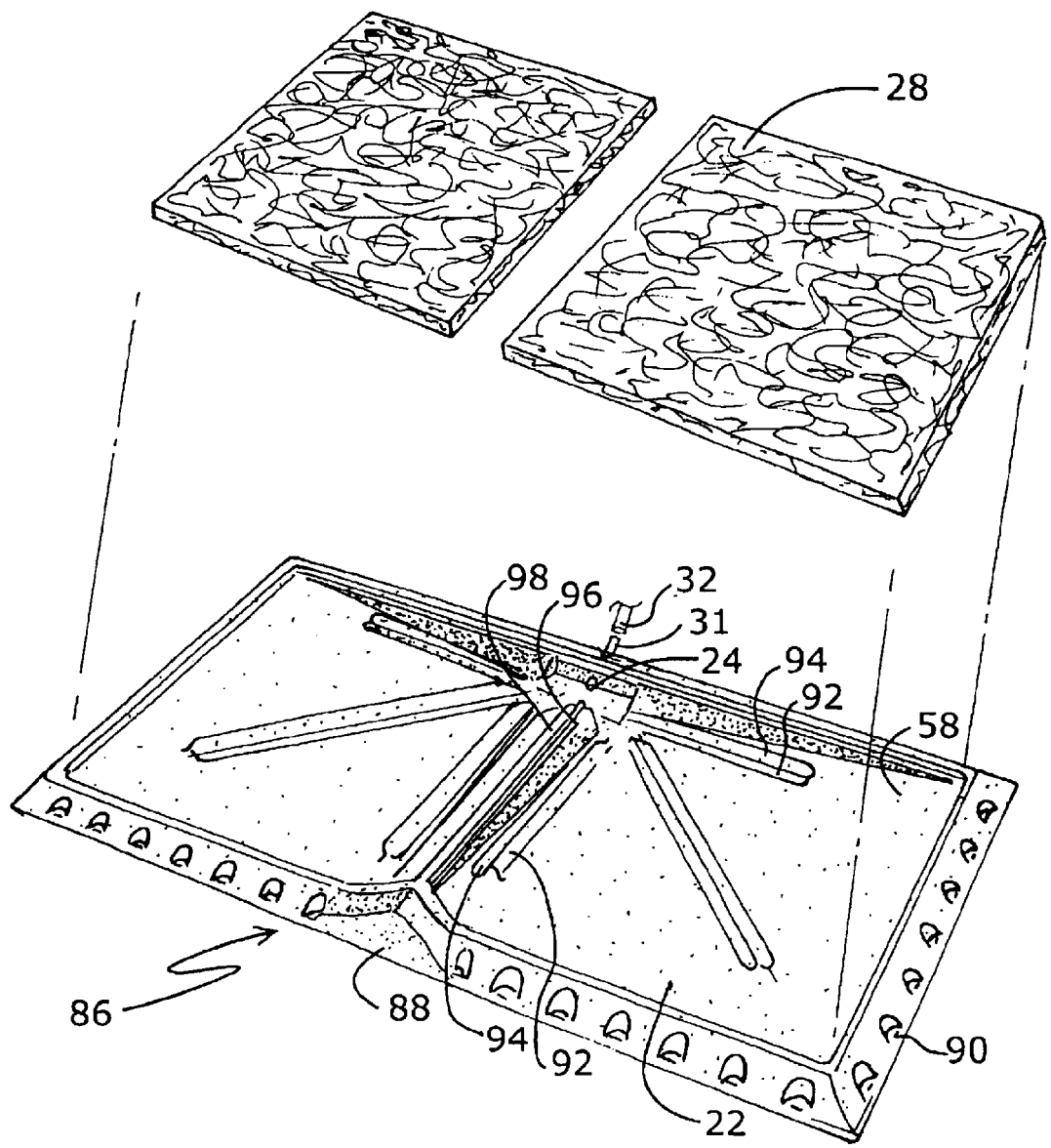
FIG. 12 is an exploded perspective view of a fourth embodiment of a folding disposable fluid control island.

FIG. 12 is an exploded perspective view of an alternative sheet-formed embodiment 86 of the folding disposable fluid control island. It is possible to vacuum-form the island bottom portion 22 from stock comprising ⅛" polymer such as closed cell low density polyethylene foam. Of course, other materials may be used equivalently including most non-absorbent sheet materials, especially sheet metals, sheet plastics, and composites. Closed-cell foam has the advantages of being light-weight, non-absorbent, relatively inexpensive, and readily disposable. The technique of vacuum forming is relatively inexpensive for short production runs. However, the product might be made using injection molding, particularly if production runs are longer.

The sheet-formed embodiment 86 is shown fitted with an optional toe-board 88 that allows a surgeon to re-position the fluid control island effortlessly during a procedure. Insets 90 stiffen the peripheral edge to better retain the pads 28. However, the bottom 22 is sufficiently resilient to collapse under the weight of a person's foot, a chair or cart wheel, or similar items, then return to the original position when the load is removed. Since the sheet-formed fluid control island 86 is not intended to support any load when in use, it is believed advantageous to allow it to deform when a load is applied to reduce the likelihood that the load will be tipped or unbalanced.

It can be seen that the upper surface 58 of the bottom is inclined toward the drain 24. The inclination may be maintained by one or more sets of ridges 92 and valleys 94. The ridges 92 support the pad 28 above the upper surface 58 of the bottom to reduce fluid retention in the island. A center dividing ridge 96 has shoulders 98 for supporting theses of th pad 28 at the same plane as the ridges 92. The valleys 94 make channels directed toward the drain 24 and contact the floor to support the upper surface 58 and maintain the desired inclination.

Figure 13:
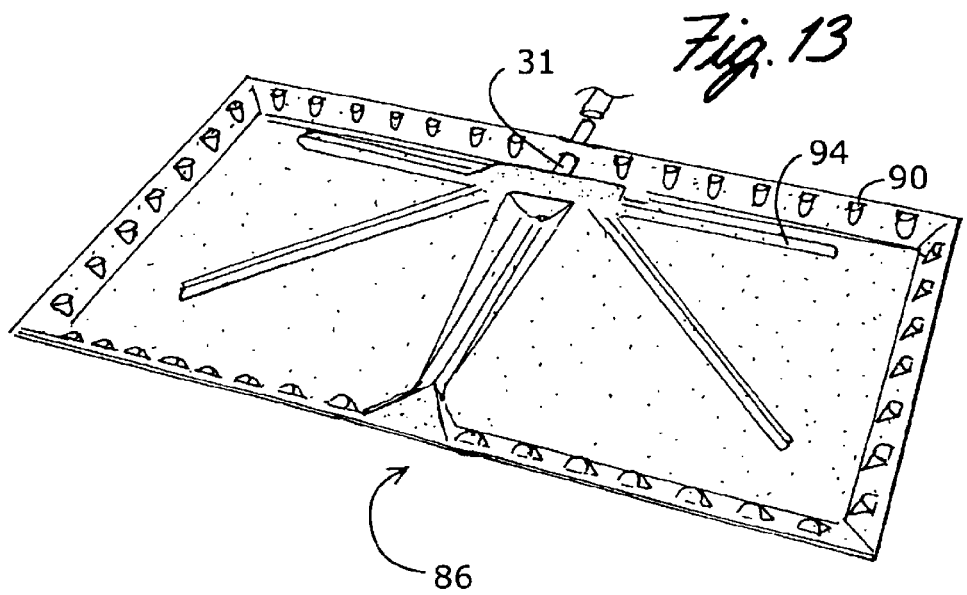
FIG. 13 is a bottom view of the disposable fluid control island base depicted in FIG. 12.

FIG. 13 is a bottom view of the disposable fluid control island 86 base depicted in FIG. 12. The floor-contacting portions of the insets 90 and valleys 94 formed in the bottom 22 can be readily seen in this view. In addition, the bulkhead feed-through 31 is easily viewed.

Figure 14:
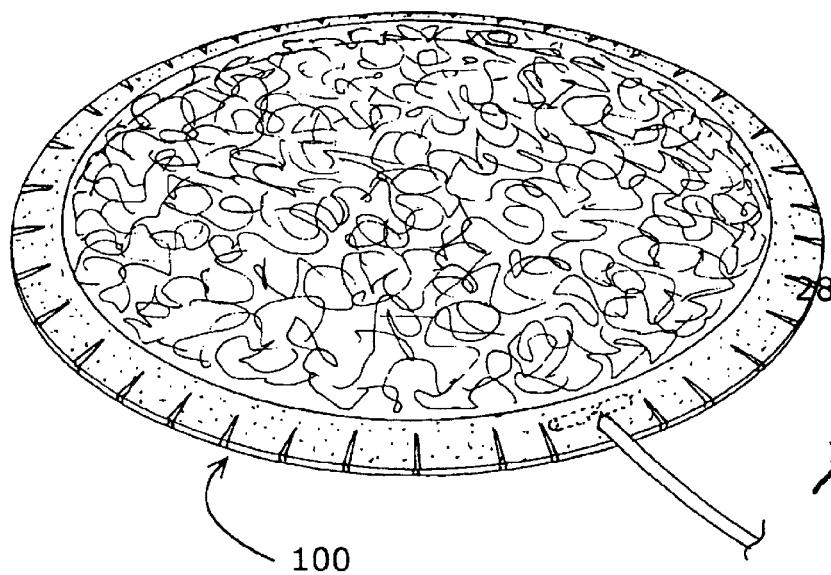
FIG. 14 is a perspective view of a fifth alternative embodiment of a fluid control island.

FIG. 14 is a perspective view of an alternative circular embodiment 100 of a fluid control island. It is possible that such a configuration will be preferred for some procedures.

A surgical drape 29 may be attached proximate the periphery of any embodiments of the vessel so as to convey fluids from an operating table to the vessel. The non-woven mesh or open-cell foam pad 28 may conveniently be placed into the vessel 22 after the drape 29 has been attached. It may be advantageous to affix the lower edge of the drape to the inner vessel peripheral wall 54 on the side of the vessel that will be closest to the operating table. The drape 29 may conveniently extend several inches along the vessel ends, perpendicular to the side of the vessel closest to the operating table, so as to channel fluids that run from the operating table and patient into the fluid control island. Adhesive portions may be incorporated onto the surgical drape 29 to retain the drape on the operating table and to hold other drape elements in the desired configuration.

Figure 15:
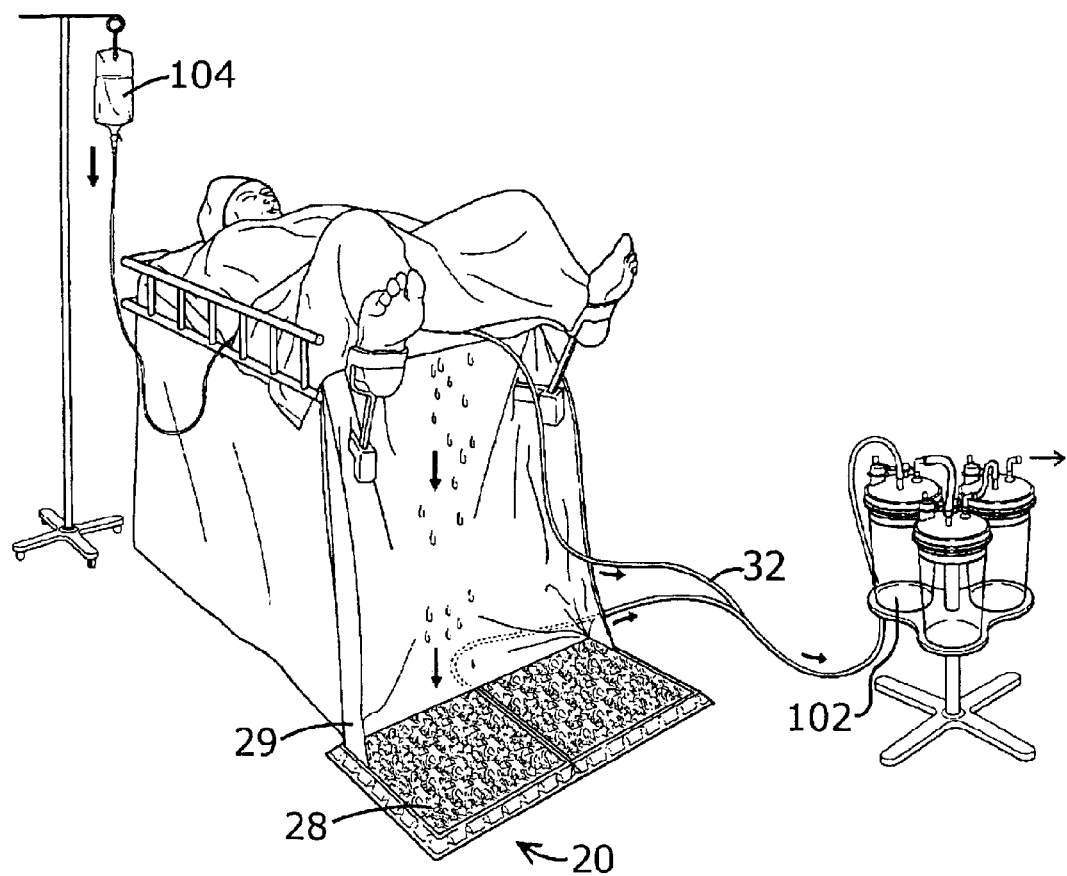
FIG. 15 is a perspective view depicting the fluid control island of FIG. 12 with vacuum-operated drain and fluid collection canisters during a surgical procedure.

FIG. 15 is a perspective view depicting the fluid control island 20 with vacuum-operated drain lines 32 linked to cascaded fluid collection canisters 102 during a surgical procedure. A fluid source 104 provides distending medium or other fluid as needed.

The fluid control island 20 and all of the alternative embodiments and all of their equivalents disclosed herein comprise a component of a system for determining the fluid balance of patients, particularly with respect to distending medium, but applicable to other fluids, as well. The system for determining patient fluid balance depicted in FIG. 15 is comprised of four main elements: means for determining the amount of fluid infused into the patient 104, means for collecting fluids received from the patient 20, means for determining the amount of fluid received from the patient 102, and means for comparing the amount of fluid received from a surgical patient to the amount of fluid infused into the patient, the arithmetic difference between the amount of fluid introduced 102 and the amount of fluid In the collection canisters 104. Present methods require Individual determinations of the volume of fluid in each container of distending medium (customarily packaged in 3 liter bags that are accurate to perhaps ±10%—far less than the accuracy needed to assure patient safety in hysteroscopic procedures).

Figure 16:
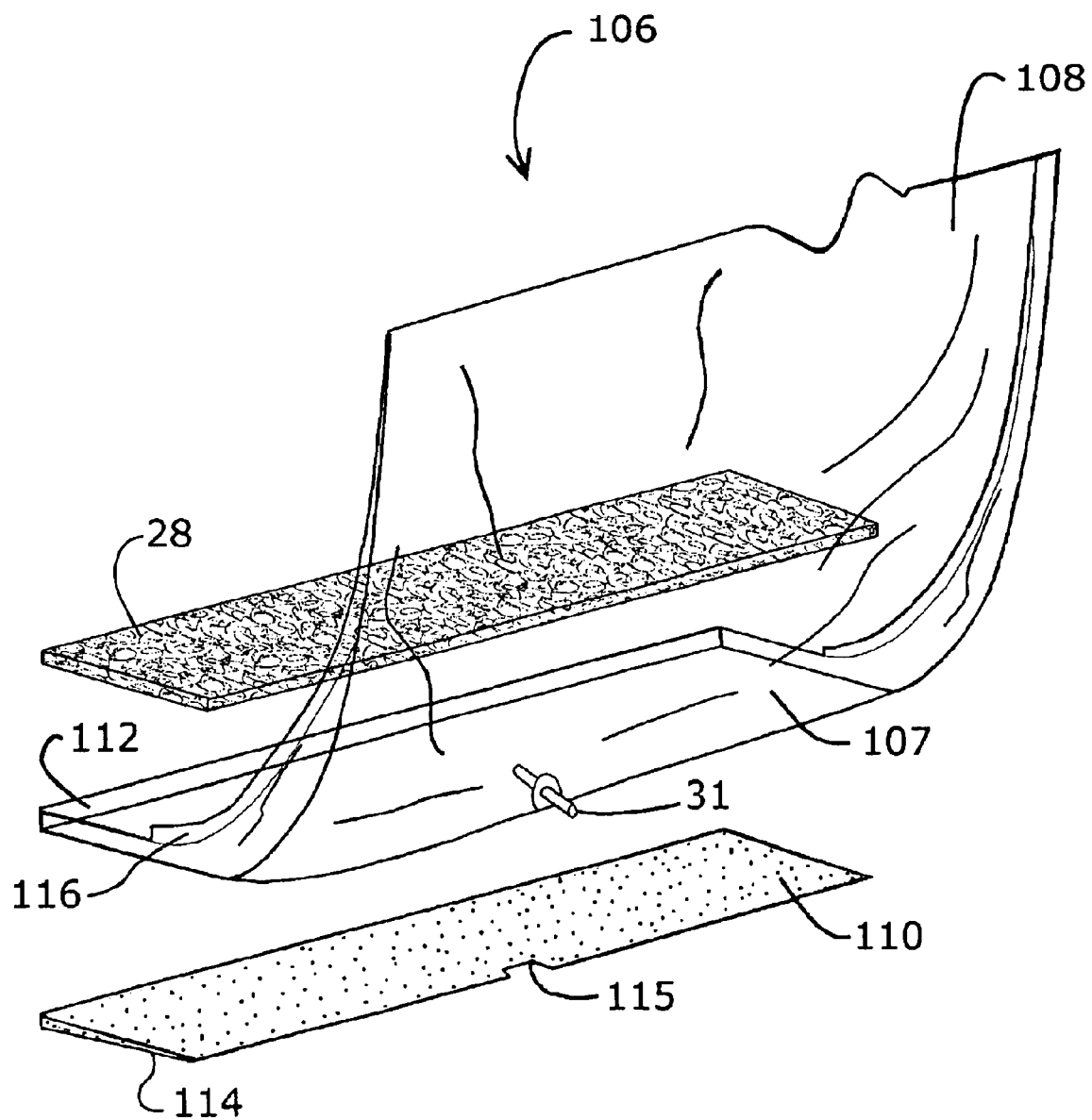
FIG. 16 shows an exploded perspective of a sixth alternative embodiment of a fluid control island viewed from a side of an operating table wherein an extension of a surgical drape is affixed to and between the upper surface of a floor-contacting foamed polymer wedge base and the lower surface of a non-woven mesh pad.

FIG. 16 is an exploded perspective view of a sixth alternative embodiment 106 of a fluid control island viewed from a location at the side of an operating room table wherein an extension of an extended surgical drape 108 is affixed to and between the upper surface of a floor-contacting foamed polymer wedge base 110 and the lower surface of a non-woven mesh pad 28. The surgical drape extension 107 thereby forms a continuous fluid-collecting surface that traverses the space from beneath the patient and the bulkhead fitting 31. It is also possible to use adhesives, mechanical fasteners, heat sealing, or other means to shape the edges of the first end of the drape extension 107 into a structure that fulfills the fluid-retaining function of peripheral edge 26 of FIG. 1 and other embodiments. The extended edges 112 of the drape may be folded up the edges of the mesh pad 28 to prevent fluids from dispersing laterally away from the collection island 106. The drape extension 107 and drape 108 may be any convenient polymer film such as a 2 mil polyethylene material having any convenient dimensions for the procedures conducted, typically 44"×73" with a nylon or other polymeric feed-through fitting 31.

The floor-contacting lower side of the polymer foam wedge 110 may optionally have anti-skid material 114 applied in situations where foot traffic may occur. The polymer foam wedge 110 may be any convenient material such as polyurethane or other low-cost material. Dimensions of this embodiment would be similar to those of other alternative embodiments previously described with a sufficient wedge gradient to cause fluid to flow to the feed-through 31 for collection (e.g. ½" per foot). A depression or cut-out 115 may be included to facilitate fluid collection by allowing the bulkhead fitting 31 to rest at the lowest point of the inclines created by supporting the drape material from the foam wedge 110 and operating table. Stiffening or shaping members 116 of elastic or springy material may be applied to enhance the fluid-collection functionality and stability of the drape 108. Heat-sealing or adhesives may be used to attach the drape extension 107 to the polymer foam wedge 110 and the mesh pad 28.

Although the drape extension 107 and drape 108 are depicted as formed integrally from a single sheet of plastic film, it is to be understood that either or both may be configured differently without departing from the invention. For example, the drape extension 107 might be formed to attach to the back of a conventional surgical drape 108 or to fit to a permanent fluid-guiding sluice affixed to an operating table. Likewise, it is possible to make this embodiment using different materials for the drape extension 107 and drape 108.

Figure 17:
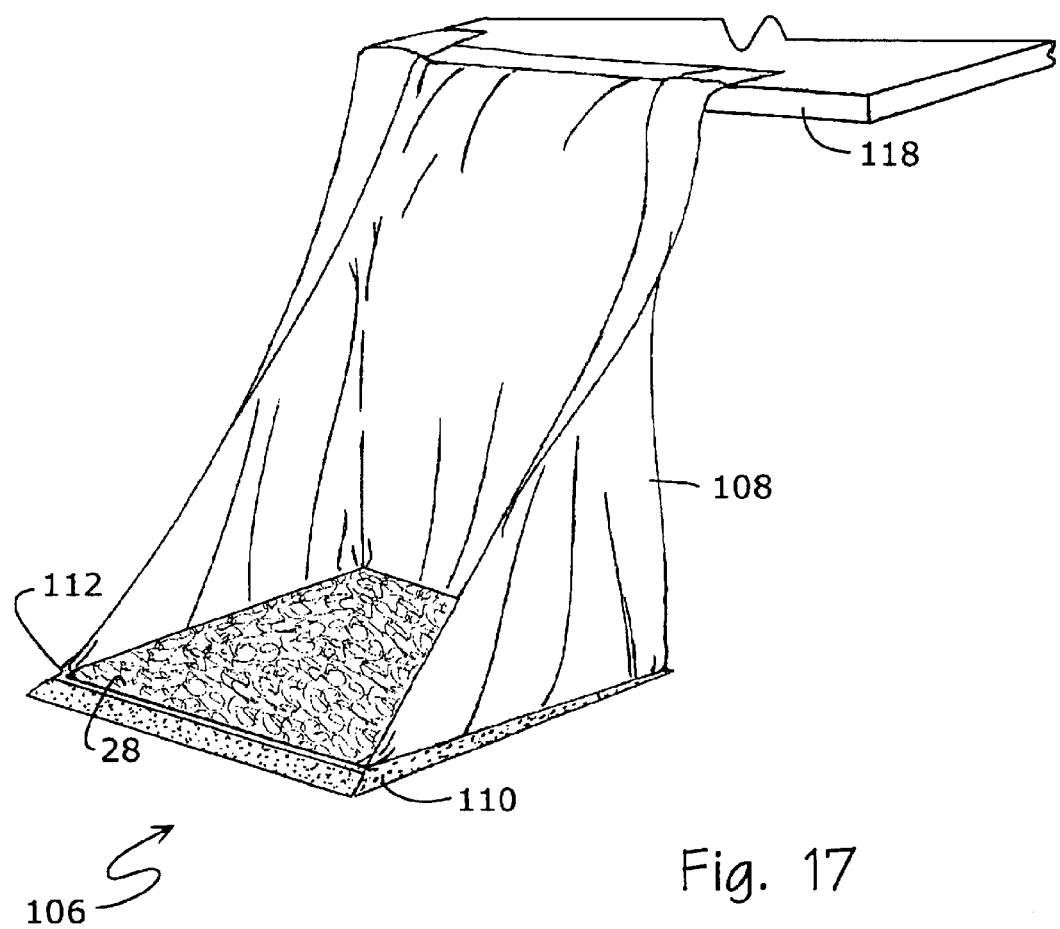
FIG. 17 shows the fluid control island of FIG. 16 fitted to an operating table viewed from a location behind the normal position of a surgeon and in which the surgical drape is configured to extend a splash barrier substantially beyond the end of the operating table.

FIG. 17 shows the fluid control island 106 of FIG. 16 fitted to an operating table viewed from a location behind the normal position of a surgeon and in which an integral combination drape extension 107 and surgical drape 108 is configured to extend a splash barrier substantially beyond the end of the operating table.

It is anticipated that the foam wedge 110 would, in most instances, have very low density such that objects such as feet or instrument stands would compress the foam sufficiently to force the drape extension 107 nearly to the elevation of the floor. It is anticipated that the incremental amount of fluid retained by the embodiment 106 due to the presence of a person standing on the mesh 28 would be negligible and would flow freely toward the drain feed-through 31 as soon as the person moved. To reduce any tendency for fluids to pool where a person may stand, it would be possible to include stiff, rod-like members disposed on the top side of the drape extension 107 below the mesh 28 perpendicular to both the narrow and the wide edges of the wedge 110 such that the weight of a person's foot would compress the foam wedge below the rod-like member, thereby forming a channel in the top side of the drape extension 107 that runs adjacent the rod-like member toward the narrow edge of the wedge 110.

It is possible to make the wedge 110 from any material or with any degree of stiffness or resilience. For example, the wedge could be made of wood, fiberboard, polystyrene, metal, etc., without departing from the scope of the invention disclosed here. It would also be possible to make the wedge 110 from any density of resilient or rigid foam. For example, it would be possible to make the wedge using expanded polystyrene bead board equivalent to the low-density resilient foam believed preferable at the present time.

Likewise, it is possible also to form the embodiment with a drain element that extends proximate, and parallel to, the narrow edge of the wedge 110. Such a drain component could be comprised of a vacuum drain tube affixed to the top side of the drape extension 107 and running along the length of the narrow edge of the wedge. Holes could be formed through the wall of the vacuum drain tube at intervals through which fluids could enter and then be conveyed by air moving toward the vacuum source and trapped collection canisters 104. It is possible that such a configuration would reduce the time required to effect collection of fluids because the distance fluid would be required to flow before reaching the vacuum collection point would be minimized. A vacuum conduit extension 64 could connect at either end or along the length of such a vacuum drain tube.

An apparatus having the elements needed to determine fluid balance holds the packaged fluids to be dispensed and the canisters that receive returned fluids on a single load cell or weight measuring scale. Ancillary equipment for pressurizing dispensed fluid and for conveying returned fluids to collection canisters may also be mounted on the device. The scale may be set to read zero when the procedure is started and to alarm in the event of a pre-determined weight loss. If desired, the system could be rinsed before zeroing the system in order to eliminate the minor effect of fluid that accumulates on wetted system surfaces. The decrease in the weight of the assembly would be directly related to the amount of fluid retained by the patient during the surgery. The scale could be calibrated to factor the density of the fluid into the amount reported so that the system could continuously display the volume of fluid retained by the patient in milliliters or other convenient units.

Other methods of determining the amounts of fluids provided to the patient include the use of metering pumps to displace distending medium from packages through the hysteroscope and into the surgical site, the use of mass flow meters to measure the amount of fluid introduced into the patient, and scales for weighing the distending medium separately from the returned fluids and/or ancillary equipment. Fluids received from the patient could be quantified likewise.

Changes and modifications in the specifically described embodiments can be carried out without departing from the scope of the invention which is intended to be limited only by the scope of the appended claims.

TABLE 1

ESTIMATES OF FLUID VOLUMES-SIMULATED OPERATING ROOM CONDITIONS

| Actual Volume | Nurse 1 estimate | Nurse 2 estimate | Nurse 3 estimate | Nurse 4 estimate | Mean of estimates | Mean of estimate errors | | Largest error | Smallest error |
|---|---|---|---|---|---|---|---|---|---|
| (ml) | (ml) | (ml) | (ml) | (ml) | (ml) | (%) | (ml) | (ml) | (ml) |
| FLUID REMAINING IN 3 LITER BAGS | | | | | | | | | |
| 2879 | 2460 | 2480 | 2500 | 2500 | 2485 | −14% | −394 | −419 | −379 |
| 1546 | 1200 | 1300 | 1350 | 1200 | 1263 | −18% | −284 | −346 | −196 |
| 2244 | 1800 | 1950 | 1800 | 1900 | 1863 | −17% | −382 | −444 | −294 |
| 1784 | 1550 | 1600 | 1800 | 1700 | 1663 | −7% | −122 | −234 | 16 |
| 843 | 525 | 575 | 600 | 500 | 550 | −35% | −293 | −343 | −243 |

TABLE 1-continued

ESTIMATES OF FLUID VOLUMES-SIMULATED OPERATING ROOM CONDITIONS

| Actual Volume (ml) | Nurse 1 estimate (ml) | Nurse 2 estimate (ml) | Nurse 3 estimate (ml) | Nurse 4 estimate (ml) | Mean of estimates (ml) | Mean of estimate errors (%) | Mean of estimate errors (ml) | Largest error (ml) | Smallest error (ml) |
|---|---|---|---|---|---|---|---|---|---|
| 1714 | 1525 | 1500 | 1500 | 1500 | 1506 | −12% | −208 | −214 | −189 |
| 1075 | 900 | 875 | 900 | 900 | 894 | −17% | −181 | −200 | −175 |
| 597 | 275 | 275 | 250 | 300 | 275 | −54% | −322 | −347 | −297 |
| 770 | 450 | 450 | 450 | 400 | 438 | −43% | −333 | −370 | −320 |
| 3114 | 2710 | 2800 | 3250 | 3000 | 2940 | −6% | −174 | −404 | −114 |
| FLUID IN KICK BUCKETS | | | | | | | | | |
| 770 | 250 | 400 | 650 | 500 | 450 | −42% | −320 | −520 | −120 |
| 1546 | 600 | 1200 | 1100 | 1000 | 975 | −37% | −571 | −948 | −346 |
| 1075 | 800 | 1000 | 900 | 1000 | 925 | −14% | −150 | −275 | −75 |
| 821 | 400 | 500 | 600 | 500 | 500 | −39% | −321 | −421 | −221 |
| FLUID ON OPERATING ROOM FLOOR | | | | | | | | | |
| 570 | 150 | 300 | 200 | 200 | 213 | −63% | −358 | −420 | −270 |
| 282 | 100 | 200 | 100 | 100 | 125 | −56% | −157 | −182 | −82 |
| 642 | 150 | 400 | 125 | 200 | 219 | −66% | −423 | −517 | −242 |
| 1115 | 300 | 600 | 275 | 300 | 369 | −67% | −746 | −840 | −515 |
| 381 | 100 | 250 | 140 | 100 | 148 | −61% | −234 | −281 | −131 |

DRAWING REFERENCE NUMBERS

- 20 disposable fluid control island
- 22 impermeable vessel bottom portion
- 24 drain portion
- 26 peripheral edge
- 28 mesh pad
- 29 surgical drape
- 30 double bi-fold fluid control island
- 31 bulkhead feed-through
- 32 conduit to collection containers
- 34 drain channels
- 36 first bottom section
- 38 second bottom section
- 40 center hinge
- 42 distal part
- 44 medial part
- 46 bottom hinge
- 48 perimeter floor-contacting base
- 50 outer wall
- 52 top surface
- 54 inner wall
- 56 panel
- 58 upper surface of bottom portion
- 60 low point
- 62 spacer
- 64 vacuum conduit extension
- 66 alternative surgical drape-equipped embodiment
- 68 "Y" connector
- 70 dual drain fluid control island
- 71 optional drain base
- 72 center drains
- 74 dividers
- 76 divider slot
- 78 divider filter block
- 80 distal portion face
- 82 medial portion face
- 84 overlap
- 86 alternative sheet-formed fluid control island
- 88 optional toe board
- 90 insets
- 92 ridge
- 94 valley
- 96 center dividing ridge
- 98 shoulder
- 100 alternative circular fluid control island
- 102 source of distending medium
- 104 fluid collection canisters
- 106 sixth alternative embodiment
- 107 drape extension
- 108 extended surgical drape
- 110 foam wedge base
- 112 rolled drape peripheral edge
- 114 optional anti-skid material
- 116 optional shaping element

What is claimed is:

1. A disposable fluid control island for selectably collecting, retaining and draining fluids received from patients during surgery comprising:
   a generally broad, shallow, impermeable vessel removably positioned on an operating room floor, the vessel having
   a generally horizontal, floor-contacting, bottom portion that is shaped to direct fluids from a patient that enter the vessel toward
   a drain portion that extends through the vessel, the drain being adapted for connection to a fluid collection container,
   a generally vertical peripheral portion, and
   a non-absorbent, non-woven, mesh pad portion fitted within the peripheral portion of the vessel and overlying the bottom portion of the vessel.

2. The apparatus defined in claim 1 wherein the drain portion is further comprised of a tubular portion communicating between the vessel and a means of conveying fluids that enter the vessel to at least one collection canister for measurement of the volume of fluids that are received by the vessel.

3. The apparatus defined in claim 1 wherein the bottom portion is inclined toward the drain.

4. The apparatus defined in claim 1 wherein the bottom portion has channels formed therein, the channels being inclined toward the drain.

5. The apparatus of claim 1 wherein a surgical drape is attached proximate the periphery of the vessel so as to convey fluids from an operating table to the vessel.

6. The apparatus of claim 2 wherein a surgical drape is attached proximate the periphery of the vessel so as to convey fluids from an operating table to the vessel.

7. The apparatus of claim 3 wherein a surgical drape is attached proximate the periphery of the vessel so as to convey fluids from an operating table to the vessel.

8. The apparatus of claim 4 wherein a surgical drape is attached proximate the periphery of the vessel so as to convey fluids from an operating table to the vessel.

9. The apparatus of claim 8 wherein the surgical drape is fitted with adhesive elements that permit the drape to be attached to an operating table.

10. The apparatus of claim 8 wherein the surgical drape is fitted with adhesive elements that permit the drape to be attached to other surgical drapes.

11. A disposable fluid control island for selectably collecting, retaining and draining fluids received from patients during surgery comprising:
a generally broad, shallow, impermeable vessel to be placed on an operating room floor, the vessel having
a generally horizontal, floor-contacting, bottom portion that is sloped to direct fluids from a patient that enter the vessel toward,
a drain portion that extends through the vessel, the drain being adapted for connection to a tubular portion communicating between the vessel and a means of conveying fluids that enter the vessel to at least one collection canister for measurement of the volume of fluids that are received by the vessel,
a generally vertical peripheral portion, and
a non-absorbent, non-woven, mesh pad portion fitted within the peripheral portion of the vessel and overlying the bottom portion of the vessel.

12. The apparatus of claim 11 wherein a surgical drape is attached proximate the periphery of the vessel so as to convey fluids from an operating table to the vessel.

13. A method for making a disposable fluid control island for selectably collecting, retaining and measuring the volume of fluids received from surgical patients during surgical procedures comprising the steps of:
forming a generally broad, shallow, impermeable vessel that is removably positioned on an operating room floor, the vessel having a generally horizontal, floor-contacting, bottom portion that is inclined toward a drain, and a generally vertical peripheral portion,
fitting a non-absorbent, non-woven, mesh pad portion within the peripheral portion of the vessel and overlying the bottom portion of the vessel,
fitting a fluid-conducting drain through the vessel, the drain being equipped with means for connection to a conduit intermediate the drain and at least one fluid collection container,
connecting a fluid conduit between the drain and a fluid collection container, the fluid collection container being fitted with means for measuring the volume of fluid contained therein, and
conveying fluid collected in the vessel from a patient through the conduit to the fluid collection vessel.

14. The method of claim 13 further comprising the step of affixing a surgical drape to the vessel proximate the vertical peripheral portion.

15. The method of claim 14 further comprising means for measuring the volume of fluid infused into a patient during a surgical procedure.

16. A system for continuously determining the volume of distending medium present within a surgical patient during a surgical procedure comprised of:
a disposable fluid control island for selectably collecting, retaining and draining fluids received from surgical patients, the island having
a generally broad, shallow, impermeable vessel, the vessel having
a generally horizontal, floor-contacting, bottom portion that is sloped to direct fluids that enter the vessel toward,
a drain portion that extends through the vessel, the drain being adapted for connection to a tubular portion communicating between the vessel and a means of conveying fluids that enter the vessel to at least one collection canister for measurement of the volume of fluids that are received by the vessel,
a generally vertical peripheral portion,
a non-absorbent, non-woven, mesh pad portion fitted within the peripheral portion of the vessel and overlying the bottom portion of the vessel,
a surgical drape affixed to the vessel proximate the vertical peripheral portion,
means for conveying fluids from the vessel to fluid collection containers and for measuring the volume of fluid collected therein, and
means for measuring the volume of distending medium infused into a surgical patient during surgery.

17. The apparatus defined in claim 16 further comprising means for comparing the volume of fluid received from a surgical patient to the volume of distending medium infused into the patient.

18. A method for continuously determining the volume of distending medium present within a surgical patient during a surgical procedure comprised the steps of:
positioning a surgical drape below and around a patient to direct fluids discharged from the patient to a disposable fluid control island for selectably collecting, retaining and draining fluids received from surgical patients, the island having
a generally broad, shallow, impermeable vessel, the vessel having
a generally horizontal, floor-contacting, bottom portion that is sloped to direct fluids that enter the vessel toward,
a drain portion that extends through the vessel, the drain being adapted for connection to a tubular portion communicating between the vessel and a means of conveying fluids that enter the vessel to at least one collection canister for measurement of the volume of fluids that are received by the vessel,
a generally vertical peripheral portion,
a non-absorbent, non-woven, mesh pad portion fitted within the peripheral portion of the vessel and overlying the bottom portion of the vessel,
a surgical drape affixed to the vessel proximate the vertical peripheral portion,
introducing measured amounts of distending medium into a patient during a surgical procedure, collecting fluids discharged from the patient in the vessel, conveying fluids from the vessel to fluid collection containers, measuring the amount of fluid collected in the fluid collection containers, measuring the difference between in the amount of distending medium infused into a surgical patient during surgery and the amount of fluid recovered from the patient.

19. A disposable fluid control island for selectably collecting, retaining and draining fluids received from patients during hysterocopic surgery comprising:

a foam wedge base having a laterally elongated, floor-contacting planar face and a laterally elongated planar upper face formed at an acute angle to the floor-contacting face;

a generally moisture-impermeable, flexible, sheet-material surgical drape extension having a top side and a bottom side, a first end portion bottom side being affixed generally coplanar to the wedge base upper face and a second end portion extendible toward a surgical operating table;

a non-absorbent, non-woven, mesh pad portion having an upper side and a lower side, the lower side being affixed generally coplanar to the top side of the surgical drape extension first end;

means for operatively interconnecting the surgical drape extension second end portion with an operating table surgical drape, and;

means for evacuating fluids from the surgical drape extension top side.

20. The apparatus of claim 19 further comprising:

a drain affixed to the surgical drape extension proximate the acute angle of the foam wedge, the drain being adapted for connection to a tubular portion communicating between the surgical drape extension top side and a means of conveying fluids that contact the surgical drape top side to at least one collection canister for the measurement of the volume of fluids that are received by the surgical drape extension.

21. Apparatus, comprising:

a non-absorbent splash-arresting pad formed of macro porous material to receive spilled fluid passing there through during a surgical procedure while providing a substantially dry and non slip support surface for surgical personnel;

a fluid impervious base having a floor and a raised peripheral edge providing an inner wall to define fluid collecting vessel to support the pad and to collect fluid passing through the pad; and a fitting projecting through the peripheral edge of the base to allow fluid collected by the vessel to be extracted.

22. The apparatus of claim 21, wherein the floor of the base is angled to move fluid collected thereon to a collection location.

23. The apparatus of claim 22, wherein the collection location is closely adjacent the fitting.

24. The apparatus of claim 22, wherein the collection location is positioned substantially the center of the floor.

25. The apparatus of claim 21 wherein tubing is coupled to the fitting and positioned on the floor of the base to convey fluid from the collection location to the fitting.

26. The apparatus of claim 21, wherein a channel is formed in the floor of the base to convey fluid from the collection location to the fitting.

27. The apparatus of claim 21, wherein a means for conveying fluid is provided to move fluid from the floor of the base toward the fitting.

28. The apparatus of claim 27, wherein the means for conveying fluid is tubing coupled to the fitting and positioned on the floor of the base to convey fluid from the collection location to the fitting.

29. The apparatus of claim 27, wherein the means for conveying fluid is a channel formed in the floor of the base to convey fluid from the collection location to the fitting.

30. The apparatus of claim 21, wherein the floor has depressions providing fluid flow channels.

31. The apparatus of claim 30, wherein ridges are formed on the floor generally aligned with and adjacent to some of the fluid flow channels.

32. The apparatus of claim 21, wherein the base is formed of pliable material and the apparatus is foldable for shipping and disposal.

33. The apparatus of claim 32, wherein the pliable material is closed cell low density polyethylene foam.

34. The apparatus of claim 32, wherein the pliable material is foamed polyurethane.

35. The apparatus of claim 21, wherein the base is hinged to facilitate folding the apparatus.

36. The apparatus of claim 35, wherein the base is hinged at multiple points to facilitate folding the apparatus.

37. The apparatus of claim 21, wherein the raised peripheral edge has a top surface having a gentle slope from the outer edge to the inner wall.

38. The apparatus of claim 37, wherein the top surface of the raised peripheral edge has insets formed therein to stiffen the base to better support the pad.

39. The apparatus of claim 21, wherein the base and pad are formed of pliable material sufficiently resilient to partially collapse under the weight of person standing on the apparatus.

40. The apparatus of claim 21, wherein at least two fittings are provided for connection to a Y connector to couple the fitting to a vacuum connection to remove fluid form the apparatus.

41. The apparatus of claim 21, also comprising a surgical drape having one end adjacent a surgical site and another end to attach to the inner wall to channel spilled fluid into the apparatus.

42. The apparatus of claim 41, wherein the surgical drape is taped to the inner wall of the base.

43. The apparatus of claim 21, also comprising a surgical drape positioned to channel spilled fluid from an operating site into the apparatus.

44. The apparatus of claim 21, also comprising an intermediate frame structure to receive the pad prior to its assembly with the base.

* * * * *

UNITED STATES PATENT AND TRADEMARK OFFICE
CERTIFICATE OF CORRECTION

PATENT NO. : 6,938,639 B1
DATED : September 6, 2005
INVENTOR(S) : Robinson

It is certified that error appears in the above-identified patent and that said Letters Patent is hereby corrected as shown below:

Column 19,
Line 12, delete "hysterocopic" and insert -- hysteroscopic --.
Line 60, after "claim 22" delete ",".

Signed and Sealed this

Fourteenth Day of February, 2006

JON W. DUDAS
*Director of the United States Patent and Trademark Office*